United States Patent
Browning et al.

(10) Patent No.: US 9,630,028 B2
(45) Date of Patent: Apr. 25, 2017

(54) ULTRASOUND SYSTEM FOR CEREBRAL BLOOD FLOW IMAGING AND MICROBUBBLE-ENHANCED BLOOD CLOT LYSIS

(75) Inventors: Theodore J. Browning, Lake Forest Park, WA (US); William Shi, Braircliff Manor, NY (US); Jeffry E. Powers, Bainbridge Island, WA (US); Michalakis Averkiou, Nicosia (CY); Thomas Gauthier, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 1677 days.

(21) Appl. No.: 12/376,317

(22) PCT Filed: Aug. 3, 2007

(86) PCT No.: PCT/IB2007/053073
§ 371 (c)(1),
(2), (4) Date: Feb. 4, 2009

(87) PCT Pub. No.: WO2008/017997
PCT Pub. Date: Feb. 14, 2008

(65) Prior Publication Data
US 2010/0160779 A1    Jun. 24, 2010

Related U.S. Application Data

(60) Provisional application No. 60/822,106, filed on Aug. 11, 2006.

(51) Int. Cl.
*A61N 7/00* (2006.01)
*A61B 8/00* (2006.01)
(Continued)

(52) U.S. Cl.
CPC ............ *A61N 7/00* (2013.01); *A61B 5/02007* (2013.01); *A61B 5/6814* (2013.01); *A61B 8/06* (2013.01);
(Continued)

(58) Field of Classification Search
CPC .... A61N 7/00; A61B 8/4227; A61B 5/02007; A61B 8/0808; A61B 8/06; A61B 8/483;
(Continued)

(56) References Cited

U.S. PATENT DOCUMENTS 5,474,073 A * 12/1995 Schwartz et al. ............. 600/456
5,558,092 A * 9/1996 Unger et al. ................. 600/439
(Continued)

OTHER PUBLICATIONS

Martin, P. J., et al., "Color-Coded Ultrasound Diagnosis of Vascular Occlusion in Acute Ischemic Stroke," Journal Neuroimaging, vol. 5, No. 3, Jul. 1995, pp. 152-156.
(Continued)

*Primary Examiner* — Long V Le
*Assistant Examiner* — Angela M Hoffa

(57) ABSTRACT

An ultrasonic diagnostic imaging system is described which utilizes one or more transducer arrays affixed to the head of a patient to diagnose and treat stroke victims. The transducer headset produces a two or three dimensional image of the vasculature inside the cranium, preferably assisted by a microbubble contrast agent. A vascular flow map is produced by the system which may be diagnosed for signs of a blood clot. If a blood clot is detected, a therapeutic beam is transmitted while the contrast agent is present to break up the blood clot by the disruption of microbubbles. The headset may also be used in a monitoring application to detect the recurrence of blood clots in a stroke victim.

20 Claims, 6 Drawing Sheets

(51) Int. Cl.
*A61B 5/02* (2006.01)
*A61B 5/00* (2006.01)
*A61B 8/06* (2006.01)
*A61B 8/13* (2006.01)
*A61B 8/08* (2006.01)

(52) U.S. Cl.
CPC .............. *A61B 8/0808* (2013.01); *A61B 8/13* (2013.01); *A61B 8/4227* (2013.01); *A61B 8/481* (2013.01); *A61B 8/483* (2013.01); *A61B 8/08* (2013.01); *A61B 8/4281* (2013.01); *A61B 8/488* (2013.01)

(58) Field of Classification Search
CPC ......... A61B 5/6814; A61B 8/481; A61B 8/13; A61B 8/08; A61B 8/4281; A61B 8/488
See application file for complete search history.

(56) References Cited

U.S. PATENT DOCUMENTS

| | | | | |
|---|---|---|---|---|
| 5,827,204 | A * | 10/1998 | Grandia et al. | 601/2 |
| 5,997,479 | A * | 12/1999 | Savord et al. | 600/447 |
| 6,013,032 | A * | 1/2000 | Savord | 600/443 |
| 6,113,547 | A * | 9/2000 | Catallo et al. | 600/459 |
| 6,171,246 | B1 * | 1/2001 | Averkiou et al. | 600/458 |
| 6,196,972 | B1 * | 3/2001 | Moehring | 600/454 |
| 6,428,477 | B1 * | 8/2002 | Mason | 600/437 |
| 6,468,219 | B1 * | 10/2002 | Njemanze | 600/454 |
| 6,503,202 | B1 * | 1/2003 | Hossack et al. | 600/454 |
| 6,524,249 | B2 * | 2/2003 | Moehring et al. | 600/438 |
| 6,612,988 | B2 * | 9/2003 | Maor et al. | 600/439 |
| 6,623,432 | B2 * | 9/2003 | Powers et al. | 600/447 |
| 6,682,483 | B1 * | 1/2004 | Abend et al. | 600/437 |
| 7,037,267 | B1 * | 5/2006 | Lipson et al. | 600/454 |
| 7,128,713 | B2 * | 10/2006 | Moehring et al. | 600/453 |
| 7,206,257 | B1 * | 4/2007 | Meng | 367/137 |
| 7,399,279 | B2 * | 7/2008 | Abend et al. | 600/450 |
| 7,425,198 | B2 * | 9/2008 | Moehring et al. | 600/454 |
| 7,534,209 | B2 * | 5/2009 | Abend et al. | 600/454 |
| 7,547,283 | B2 * | 6/2009 | Mourad et al. | 600/459 |
| 7,662,098 | B2 * | 2/2010 | Kubota et al. | 600/439 |
| 7,686,763 | B2 * | 3/2010 | Vaezy et al. | 600/439 |
| 7,717,853 | B2 * | 5/2010 | Nita | 600/466 |
| 7,828,754 | B2 * | 11/2010 | Furuhata et al. | 601/2 |
| 7,857,763 | B2 * | 12/2010 | Tai | 600/437 |
| 7,896,821 | B1 * | 3/2011 | Magnin et al. | 601/2 |
| RE42,803 | E * | 10/2011 | Lipson et al. | 600/454 |
| 8,057,408 | B2 * | 11/2011 | Cain et al. | 601/2 |
| 8,211,023 | B2 * | 7/2012 | Swan et al. | 600/457 |
| 8,366,620 | B2 * | 2/2013 | Nita | 600/437 |
| 2002/0198469 | A1 * | 12/2002 | Bridger et al. | 600/586 |
| 2004/0019278 | A1 * | 1/2004 | Abend | 600/454 |
| 2004/0049134 | A1 | 3/2004 | Tosaya et al. | |
| 2004/0220474 | A1 * | 11/2004 | Abend et al. | 600/437 |
| 2004/0267127 | A1 * | 12/2004 | Abend et al. | 600/450 |
| 2005/0004461 | A1 * | 1/2005 | Abend | 600/437 |
| 2005/0015009 | A1 | 1/2005 | Mourad et al. | |
| 2005/0033174 | A1 * | 2/2005 | Moehring et al. | 600/453 |
| 2005/0038342 | A1 * | 2/2005 | Mozayeni et al. | 600/454 |
| 2005/0075568 | A1 * | 4/2005 | Moehring | 600/453 |
| 2005/0085748 | A1 * | 4/2005 | Culp et al. | 601/2 |
| 2006/0173321 | A1 * | 8/2006 | Kubota et al. | 600/439 |
| 2006/0184070 | A1 * | 8/2006 | Hansmann et al. | 601/2 |
| 2007/0016040 | A1 * | 1/2007 | Nita | 600/439 |
| 2007/0016046 | A1 * | 1/2007 | Mozayeni et al. | 600/443 |
| 2007/0016050 | A1 * | 1/2007 | Moehring et al. | 600/454 |
| 2007/0038100 | A1 * | 2/2007 | Nita | 600/439 |
| 2008/0262350 | A1 * | 10/2008 | Unger | 600/439 |
| 2008/0269609 | A1 * | 10/2008 | Abend et al. | 600/440 |
| 2010/0069797 | A1 * | 3/2010 | Cain et al. | 601/2 |
| 2012/0010541 | A1 * | 1/2012 | Cain et al. | 601/2 |

OTHER PUBLICATIONS

Becker, G., et al., "Transcranial Color-Coded Real-Time Sonography of Intracranial Veins," Journal of Neuroimaging, vol. 5, No. 2, Apr. 1995, pp. 87-94.

Reis, F., "Clinical Experience with Echo-Enhanced Transcranial Doppler and Duplex Imaging," Journal of Neuroimaging Suppl. 1 to vol. 7, Apr. 1997, pp. S15-S21.

Nabavi, D. G., et al., "Diagnostic Benefit of Enchocontrast Enhancement for the Insufficient Transtemporal Bone Window," Journal of Neuroimaging, vol. 9, No. 2, Apr. 1999, pp. 102-107.

Seidel, G., et al., "Harmonic Grey Scale Imaging of the Human Brain," Journal of Neuroimaging, vol. 9, No. 3, Jul. 1999, pp. 171-174.

Akiyama, M., et al., "Low-Frequency Ultrasound Penetrates the Cranium and Enhances Thrombolysis in Vitro," Neurosurgery, vol. 43, No. 4, Oct. 1998, pp. 828-833.

Olsson, S. B., et al., "Enhancement of Thrombolysis by Ultrasound," Ultrasound in Med. & Biol., vol. 20, No. 4, pp. 375-382, 1994.

Alexandrov, A. V., et al., "High Rate of Complete Recanalization and Dramatic Clinical Recovery During tPA Invusion When Continuously Monitored with 2-MHz Transcranial Doppler Monitoring," http://stroke.ahajournals.org/cgi/content/full/31/3/610, Stroke, vol. 31, pp. 610-614, 2000.

Luo, H., et al., "Myocardial Ischemia/Infarction/Thrombolysis: Transcutaneous Ultrasound Augments Lysis of Arterial Thrombi In Vivo," Circulation, vol. 94(4), Aug. 15, 1996, pp. 775-778; http://gateway.ut.ovid.com/gw1/ovidweb.cgi (pp. 1-14).

Abstracts, Journal of Neuroimaging, 1997, vol. 7, pp. 229-230.

* cited by examiner

ULTRASOUND SYSTEM FOR CEREBRAL BLOOD FLOW IMAGING AND MICROBUBBLE-ENHANCED BLOOD CLOT LYSIS

This application claims the benefit of International Application PCT/IB07/53073, filed on Aug. 3, 2007, which in turn claims the benefit of U.S. provisional patent application Ser. No. 60/822,106 filed on Aug. 11, 2006.

This invention relates to medical diagnostic ultrasound systems and, in particular, to ultrasound systems which perform imaging and therapy for stroke victims.

Ischemic stroke is one of the most debilitating disorders known to medicine. The blockage of the flow of blood to the brain can rapidly result in paralysis or death. Attempts to achieve recanalization through thrombolytic drug therapy such as treatment with tissue plasminogen activator (tPA) has been reported to cause symptomatic intracerebral hemorrhage in a number of cases. Advances in the diagnosis and treatment of this crippling affliction are the subject of continuing medical research.

Transcranial Doppler ultrasound has been developed for use in monitoring and diagnosing stroke. A headset device manufactured by Spencer Technologies of Seattle, Wash., USA holds two transducers against the side of the skull, one on each temporal bone just in front of the ear. The transducers transmit ultrasonic waves through the temporal bone and the returning echo signals are Doppler processed and the phase shift information reproduced at audible frequencies. The audible Doppler identifies the presence or absence of blood flow inside the cranium as the clinician listens for characteristic sounds of blood flow velocities of specific arteries. The technique can also be augmented with a spectral Doppler display of the phase shift information, providing information on flow velocities inside the cranium. However, since there is no information concerning the anatomy inside the skull, the clinician must attempt to make a diagnosis on the basis of this limited information. This diagnostic approach is also very technique-dependent and is performed by highly trained individuals.

Recently Dr. Andrei Alexandrov of the University of Texas Medical School at Houston, Tex. found that the application of ultrasound during tPA treatment improved the efficacy of tPA for stroke treatment. Dr. Alexandrov observed that the micro-vibrations of the ultrasonic waves work on the surface of the blood clot to open up a larger surface that the tPA can then bind to and penetrate. Dr. Alexandrov is now leading a research team which is investigating the added efficacy of adding ultrasonic contrast agent microbubbles to the tPA or using microbubbles and ultrasound alone to dissolve blood clots. It is also contemplated that microbubbles may be targeted to components in the blood clot such as fibrin and stick to the clot, increasing the concentration and effectiveness of the treatment. Targeted nanoparticles are another possibility for this procedure. It is thus believed by many that ultrasound together with thrombolytic drugs, microbubbles, or both can lead to significant improvement in stroke treatment.

In accordance with the principles of the present invention, a diagnostic ultrasound system and method are described which enable a clinician to transcranially visualize a region of the cerebral vasculature where blood clots may be present. Either two dimensional or three dimensional imaging may be employed. The imaging of the vasculature is preferably enhanced by the administration of microbubbles. If the flow conditions of the vasculature indicate the presence of a partial or complete occlusion, a focused or pencil beam is directed to the location of the blockage to break up the clot by the vibrations and/or rupturing of the microbubbles. In some instances the ruptured microbubbles may also release an encapsulated thrombolytic drug. In accordance with a further aspect of the present invention, the cranial vasculature may be monitored by ultrasonic imaging for changes which are indicative of the recurrence of an occlusion, and medical aid alerted to the condition.

Figure 1:
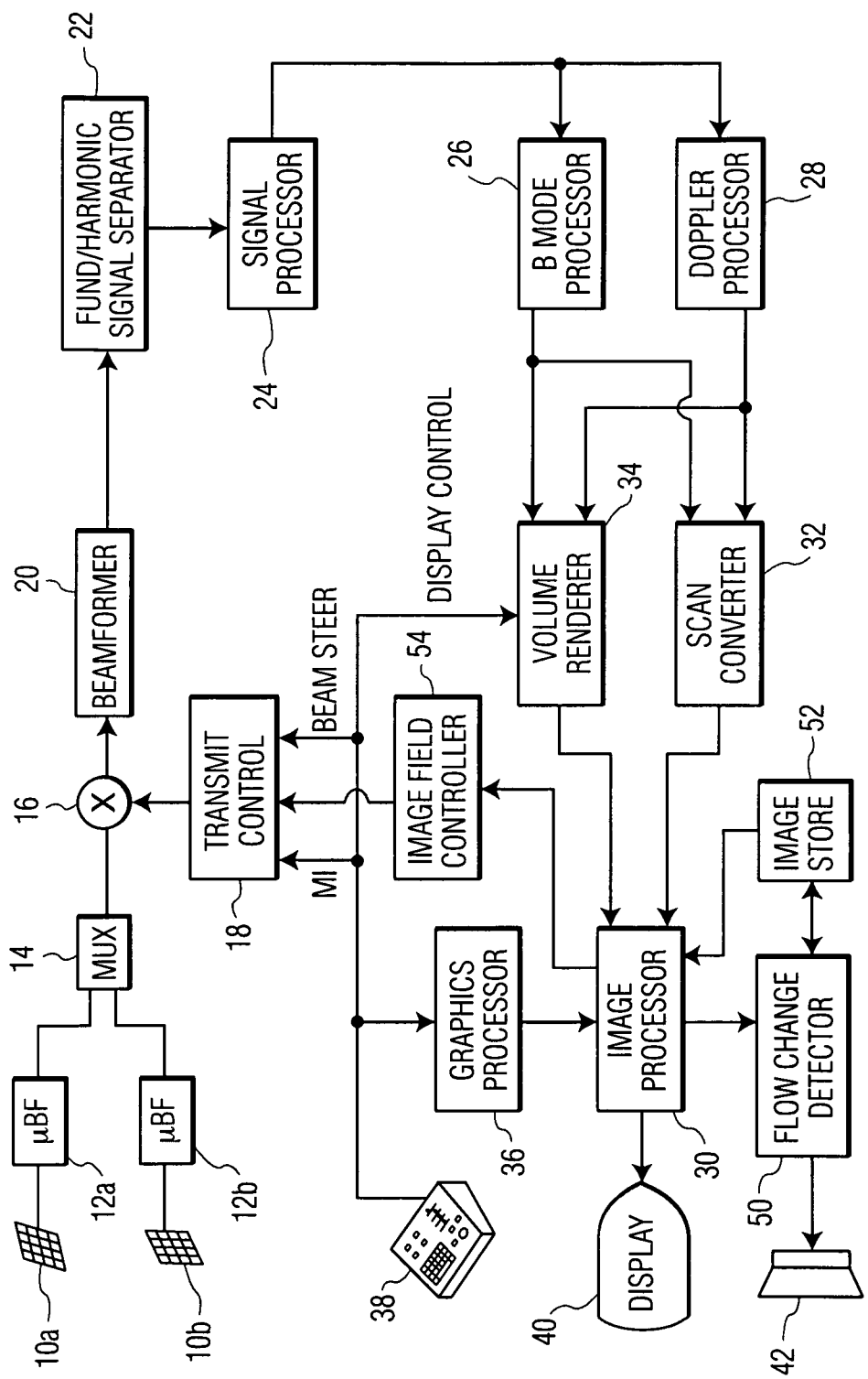
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. Two transducer arrays 10a and 10b are provided for transmitting ultrasonic waves and receiving echo information. In this example the arrays shown are two dimensional arrays of transducer elements capable of providing 3D image information although an implementation of the present invention may also use two dimensional arrays of transducer element which produce 2D (planar) images. The transducer arrays are coupled to microbeamformers 12a and 12b which control transmission and reception of signals by the array elements. Microbeamformers are also capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) Signals are routed to and from the microbeamformers by a multiplexer 14 by time-interleaving signals. The multiplexer is coupled to a transmit/receive (T/R) switch 16 which switches between transmission and reception and protects the main beamformer 20 from high energy transmit signals. The transmission of ultrasonic beams from the transducer arrays 10a and 10b under control of the microbeamformers 12a and 12b is directed by the transmit controller 18 coupled to the T/R switch, which received input from the user's operation of the user interface or control panel 38.

The partially beamformed signals produced by the microbeamformers 12a, 12b are coupled to a main beamformer 20 where partially beamformed signals from the individual patches of elements are combined into a fully beamformed signal. For example, the main beamformer 20 may have 128 channels, each of which receives a partially beamformed signal from a patch of 12 transducer elements. In this way the signals received by over 1500 transducer elements of a two dimensional array can contribute efficiently to a single beamformed signal.

The beamformed signals are coupled to a fundamental/harmonic signal separator 22. The separator 22 acts to separate linear and nonlinear signals so as to enable the identification of the strongly nonlinear echo signals returned from microbubbles. The separator 22 may operate in a variety of ways such as by bandpass filtering the received signals in fundamental frequency and harmonic frequency bands, or by a process known as pulse inversion harmonic separation. A suitable fundamental/harmonic signal separator is shown and described in international patent publication WO 2005/074805 (Bruce et al.) The separated signals are coupled to a signal processor 24 where they may undergo additional enhancement such as speckle removal, signal compounding, and noise elimination.

The processed signals are coupled to a B mode processor 26 and a Doppler processor 28. The B mode processor 26 employs amplitude detection for the imaging of structures in the body such as muscle, tissue, and blood cells. B mode images of structure of the body may be formed in either the harmonic mode or the fundamental mode. Tissues in the body and microbubbles both return both types of signals and the harmonic returns of microbubbles enable microbubbles to be clearly segmented in an image in most applications. The Doppler processor processes temporally distinct signals from tissue and blood flow for the detection of motion of substances in the image field including microbubbles. The structural and motion signals produced by these processors are coupled to a scan converter 32 and a volume renderer 34, which produce image data of tissue structure, flow, or a combined image of both characteristics. The scan converter will convert echo signals with polar coordinates into image signals of the desired image format such as a sector image in Cartesian coordinates. The volume renderer 34 will convert a 3D data set into a projected 3D image as viewed from a given reference point as described in U.S. Pat. No. 6,530,885 (Entrekin et al.) As described therein, when the reference point of the rendering is changed the 3D image can appear to rotate in what is known as kinetic parallax. This image manipulation is controlled by the user as indicated by the Display Control line between the user interface 38 and the Volume renderer 34. Also described is the representation of a 3D volume by planar images of different image planes, a technique known as multiplanar reformatting. The volume renderer 34 can operate on image data in either rectilinear or polar coordinates as described in U.S. Pat. No. 6,723,050 (Dow et al.) The 2D or 3D images are coupled from the scan converter and volume renderer to an image processor 30 for further enhancement, buffering and temporary storage for display on an image display 40.

A graphics processor 36 is also coupled to the image processor 30 which generates graphic overlays for displaying with the ultrasound images. These graphic overlays can contain standard identifying information such as patient name, date and time of the image, imaging parameters, and the like, and can also produce a graphic overlay of a beam vector steered by the user as described below. For this purpose the graphics processor received input from the user interface 38. The user interface is also coupled to the transmit controller 18 to control the generation of ultrasound signals from the transducer arrays 10a and 10b and hence the images produced by and therapy applied by the transducer arrays. The transmit parameters controlled in response to user adjustment include the MI (Mechanical Index) which controls the peak intensity of the transmitted waves, which is related to cavitational effects of the ultrasound, steering of the transmitted beams for image positioning and/or positioning (steering) of a therapy beam as discussed below.

Figure 2A:
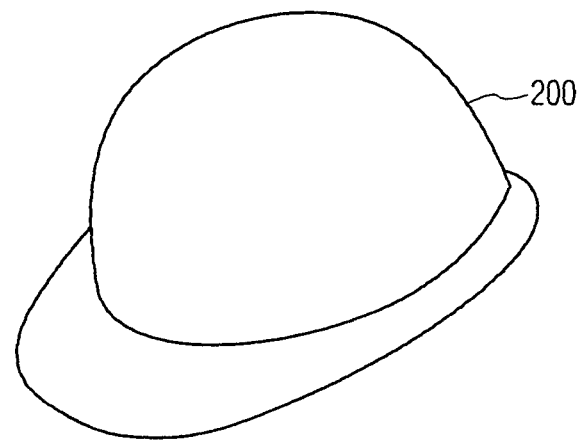
FIGS. 2a and 2b illustrate a safety helmet liner suitable for use in a transcranial imaging transducer headset.
Figure 2B:
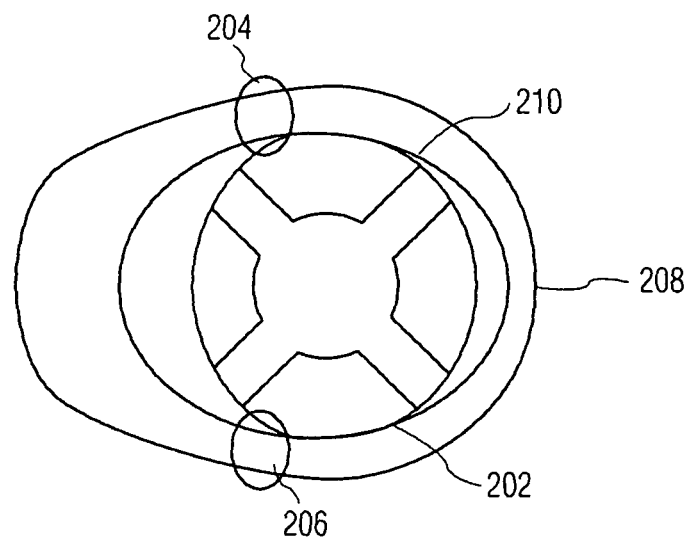

The transducer arrays 10a and 10b transmit ultrasonic waves into the cranium of a patient from opposite sides of the head, although other locations may also or alternately be employed such as the front of the head or the sub-occipital acoustic window at the back of the skull. The sides of the head of most patients advantageously provide suitable acoustic windows for transcranial ultrasound at the temporal bones around and above the ears on either side of the head. In order to transmit and receive echoes through these acoustic windows the transducer arrays must be in good acoustic contact at these locations which may be done by holding the transducer arrays against the head with a headset. For instance, FIG. 2a shows a conventional safety helmet 200 which is adjustably held on the wearer's head by a helmet liner 202 shown in the view of FIG. 2b. The helmet liner wraps securely about the circumference of the wearer's head. Transducer arrays positioned inside the helmet liner on either side as indicated by the locations of circles 204,206 will be held securely against the skin of the temporal bones of the wearer, enabling the helmet liner 202 to function as a transcranial ultrasound headset. The helmet liner headset is adjustably secured in place by an adjustment knob 208. An occipital transducer would be positioned at or below the location of adjustment knob 208. The headset has one or more straps 210 which pass over the top of the head for adjustment of the vertical position of the headset. These straps and other adjustable members of the headset can be elastic or adjustable through other means such as buckles or Velcro®. When properly adjusted the headset will hold the acoustic transducer arrays securely in good acoustic contact on the temples of the patient. Acoustic coupling may be aided by applying an acoustic coupling gel between the transducer and the skin.

Figure 3:
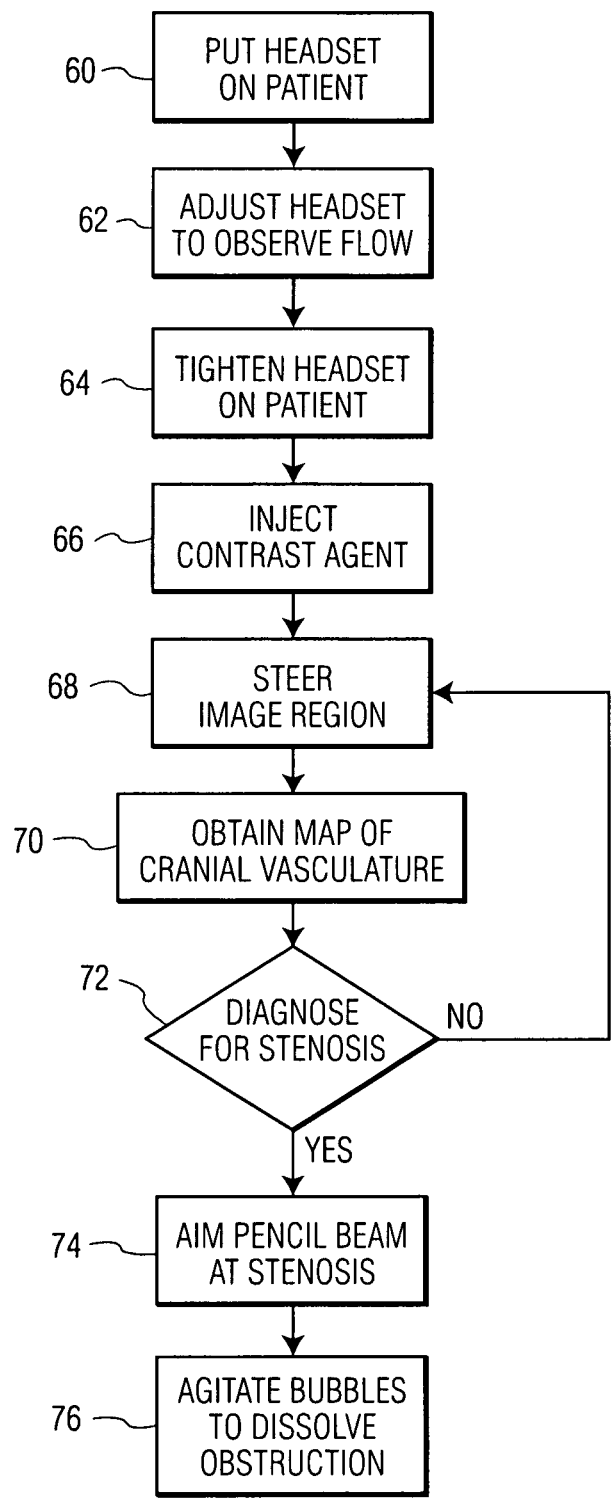
FIG. 3 illustrates a procedure for ultrasonically imaging the cranial vasculature and dissolving blood clots in accordance with the principles of the present invention.
Figure 4:
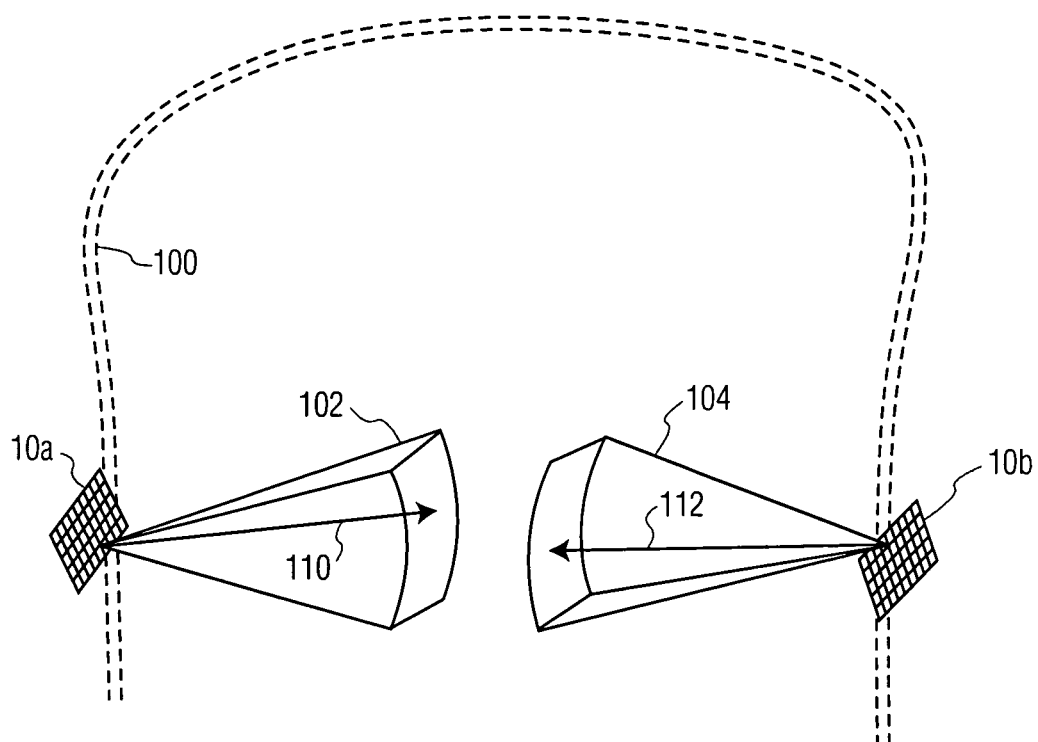
FIG. 4 illustrates three dimensional transcranial imaging in accordance with the present invention.

A procedure in accordance with the present invention which uses the ultrasound system and transcranial ultrasound headset just described is illustrated by the flowchart of FIG. 3. In step 60 the headset is put on the patient with the transducer arrays in acoustic contact with the skin of the patient. The system is activated to image inside the cranium and in step 62 the headset is adjusted until flow inside the cranium can be seen in the ultrasound image of one or (when displayed in duplex) both of the transducer arrays. The colorflow imaging mode of the system is preferably used at this time to produce a two or three dimensional image of the bloodflow inside the cranium. If the cranial flow can be seen in colorflow, the other steps of this procedure can be expected to proceed as desired. When the flow is seen in the ultrasound images the headset is tightened in step 64 to secure the transducer array in their imaging positions. FIG. 4 illustrates the situation at this point for 3D imaging. In this illustration the transducer arrays 10a,10b are held against the sides of the skull 100 and are imaging 3D image fields 102,104 inside the cranium. The user will see one or both of the 3D image fields 102,104 on the display of the ultrasound system in either a multiplanar or volume rendered 3D projection. The user can manipulate the kinetic parallax control to observe the volume rendered 3D image from different orientations. The user can adjust the relative opacity of the tissue and flow components of the 3D image to better visualize the vascular structure inside the brain tissue as described in U.S. Pat. No. 5,720,291 (Schwartz) or can turn off the B mode (tissue) portion of the display entirely and just visualize the flow of the vascular structure inside the 3D image field 102,104.

When the cranium is being imaged successfully a microbubble contrast agent is introduced into the patient's bloodstream at step 66. In a short time the microbubbles in the bloodstream will be pumped through the carotid arteries and into the cranial vascular system and appear in the image. The clinician user is now able to begin a diagnostic search for blood clots occluding blood vessels in the brain, looking for branches of the vasculature which terminate or are only dimly lighted by echo returns from microbubbles due to a partial occlusion. When a dual display from both transducer arrays is present the clinician is also able to compare the relative symmetry of the two displayed regions, looking for signs of asymmetry. If the clinician finds no signs of occlusion in the vasculature presently being viewed by the image fields 102,104, the clinician can steer the image field to other regions of the anatomy as indicated by step 68. Steering the image field can be done mechanically by physically adjusting the position of a transducer array to aim its image field through different anatomy of the brain. Preferably, the clinician is able to adjust the steering of the beams from the transducer array with a control on the user interface. By adjusting this control (the Beam Steer control line to the transmit controller 18), the clinician is able to electronically steer the image field around inside the skull without disturbing the acoustic coupling of the array against the head of the patient.

At each position of the image field 102,104 the clinician can look for obstructions of the blood flow in the real time images on the display, or can capture (freeze) an image or map of the cranial vasculature as indicated in step 70. When the vascular map is acquired and held statically, the image can undergo enhanced processing (e.g., compounding, signal averaging) to improve the resolution or scale of the image and can be manipulated on the screen and examined carefully at different points and from different views in a precise search for blood vessel occlusions. In this way the clinician can diagnose for stenoses as indicated at step 72. If the clinician examines a vascular map and finds no evidence of obstruction in the blood flow paths, the clinician can steer the image field to another region of the cranium and examine the vascular map of another image field. The clinician can use the Doppler data of the vascular map or the spectral Doppler function of the ultrasound system to take flow velocity measurements at specific points in the cranial vasculature, then use the report generation capabilities of the ultrasound system to record the measurements and prepare a report of his diagnosis.

Figure 6A:
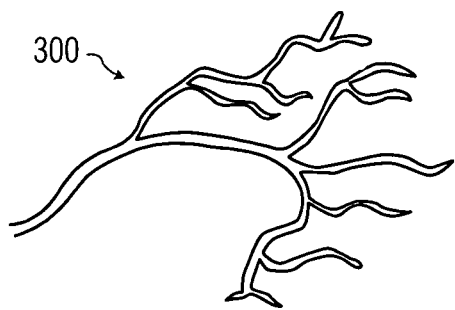
FIGS. 6a-6d illustrate treatment of a cranial occlusion in accordance with the principles of the present invention.
Figure 6B:
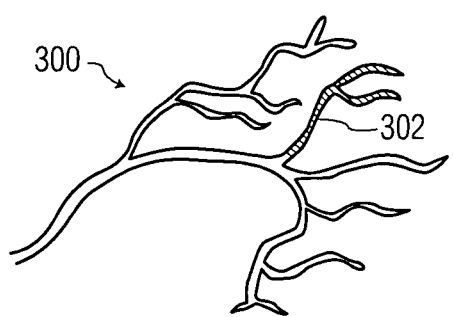
Figure 6C:
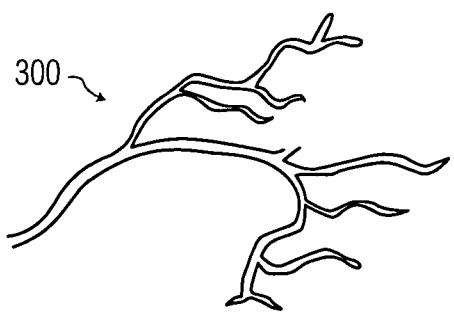
Figure 6D:
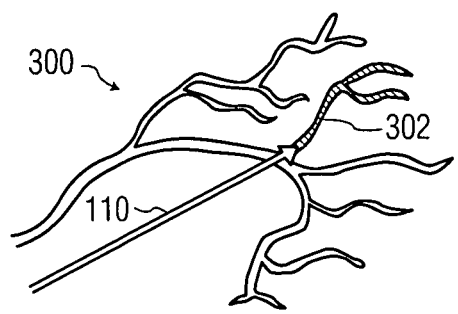

Examples of vascular maps are shown in FIGS. 6a-6c. FIG. 6a illustrates a vascular network 300 of blood vessels. When only flow imaging is performed and the flow image is displayed in the absence of any surrounding B mode tissue structure, as described in U.S. Pat. No. 5,474,073 (Schwartz et al.), only the flow of the vasculature is shown without any obscuring surrounding structure as FIG. 6a illustrates. The vascular network 300 may be displayed in two dimensions, three dimensions, and by various Doppler techniques such as colorflow (velocity) Doppler or power (intensity) Doppler. In the absence of stenoses the flow network will appear continuous and with velocities and intensities proportionate to vessel size. But if a branch 302 of the vascular network is obstructed, the flow will appear different, e.g., higher velocity and/or intensity, and, if completely obstructed, will disappear entirely in the Doppler flow map as shown in FIG. 6c. By discerning characteristics such as these, the clinician can diagnose a stenosis, then direct a therapeutic beam 110 to the suspected location of the obstruction of the vessel as shown in FIG. 6d.

If the clinician discovers a stenosis, therapy can be applied by agitating or breaking microbubbles at the site of the stenosis in an effort to dissolve the blood clot. The clinician activate the "therapy" mode, and a graphic 110,112 appears in the image field 102,104, depicting the vector path of a therapeutic ultrasound beam. The therapeutic ultrasound beam is manipulated by a control on the user interface 38 until the vector graphic 110,112 is focused at the site of the blockage, as indicated by step 74. The therapeutic beam can be a tightly focused, convergent beam or a beam with a relatively long focal length known as a pencil beam. The energy produced for the therapeutic beam can be in excess of the ultrasound levels permitted for diagnostic ultrasound, in which case the microbubbles at the site of the blood clot will be sharply broken. The energy of the resulting microbubble ruptures will strongly agitate the blood clot, tending to break up the clot and dissolve it in the bloodstream. However in some instances insonification of the microbubbles at diagnostic energy levels may be sufficient to dissolve the clot. Rather than breaking in a single event, the microbubbles may be vibrated and oscillated, and the energy from such extended oscillation prior to dissolution of the microbubbles can be sufficient to break up the clot, as indicated at step 76.

A particularly effective way to insonify the microbubbles is known as "flash" transmission. In flash transmission, insonification is halted to allow the flow of blood to deliver a substantial volume of microbubbles to the site of the blockage. At the end of this pause, a rapid series of high MI pulses are transmitted to rapidly and energetically rupture the microbubbles, which releases energy at the site of the blockage. The gas from the ruptured microbubbles dissolves in the bloodstream. Another pause period commences to allow the buildup of a fresh supply of microbubbles and the process continues. See U.S. Pat. No. 5,560,364 (Porter) and U.S. Pat. No. 5,685,310 (Porter). The flash technique was improved with the discovery that imaging can be performed at low MI levels as the microbubbles accumulate, enabling the clinician to visually monitor the buildup of microbubbles and determine the optimal time to administer the high MI flash. See U.S. Pat. No. 6,171,246 (Averkiou et al.)

In accordance with a further aspect of the present invention, it has been found that a low duty cycle flash will create rapid microbubble destruction within the energy limits of diagnostic ultrasound. There is thus no need to expose the patient to possibly harmful therapeutic exposure levels. In this technique, the flash pulses are delivered within the MI (instantaneous pressure) limits of diagnostic ultrasound. Another energy limit parameter for ultrasound is the spatial peak temporal average (SPTA), which is a measure of the average energy delivered over time and is related to temperature rise. It has been discovered that a series of high MI pulses (within diagnostic limits) will cause the targeted microbubbles to break up and dissolve in the bloodstream in 100-300 milliseconds. Thus, continued insonification is of no effect, for virtually no microbubbles remain after this period. In the inventive technique, the high MI pulse period has a duty cycle of 50% or less. For instance, the high MI pulses may be delivered for 200 ms, after which high MI pulses are inhibited for the following 800 msec. The duty cycle of the high MI pulse delivery period is thus only 20%. Needless high MI pulses are inhibited and the time averaged energy delivered over the one second interval is within the temporal average limits of the SPTA parameter. Furthermore, new microbubbles are allowed to reinfuse the blood clot site as soon as the high MI transmission has ceased. Moreover, longer pulse lengths may be employed during the high MI portion of the duty cycle, which have been found to be very effective for microbubble disruption.

The type of stroke suffered by a patient can be either hemorrhagic stroke or ischemic stroke. Hemorrhagic stroke, which may for instance be caused by a ruptured aneurism, results in blood flow outside of blood vessels and will not be improved by treatment with microbubbles and ultrasound.

Furthermore, a hemorrhagic condition is often worsened by the application of tPA. Ischemic stroke caused by a stenosis such as a blood clot is the type of stroke that an embodiment of the present invention is designed to treat. Accordingly it is desirable to initially determine whether the stroke condition is hemorrhagic or ischemic. One way this may be done is by looking for a blood pool outside the vasculature, which is indicative of a hemorrhagic condition. A blood pool will appear black in the standard ultrasound image since blood is not a strong reflector of ultrasonic waves. The blood pool may also exhibit a lower rate of flow (Doppler velocity) than the flow of blood in a containing blood vessel. After the contrast agent is introduced, the perfusion of the contrast agent into the microvasculature of surrounding tissue can create a slight halo effect of brighter contrast about the darkened blood pool in an ultrasound image. It is characteristics such as these which can be used to identify whether the stroke is hemorrhagic or ischemic in origin.

In the depiction of FIG. 4, each image field 102, 104 is seen to extend almost halfway across the cranium, which is a balance between the size of the image field and the acoustic penetration and attenuation which may be expected through the bone at the acoustic window. For some patients, low attenuation effects may enable an image field to extend fully across the cranium, allowing the clinician to examine the vascular structure near the skull bone on the opposite side of the cranium. By alternately examining image fields of both transducer arrays, the vasculature across the full cranium may be effectively examined. It is possible to acquire extended image fields which cover the same central region of the cranium but image from opposite sides of the head. These images can be correlated and compounded together, forming a fused image that may reveal additional characteristics of the brain. The therapeutic beam can also be transmitted from both sides of the head, enabling breakup of a clot at both sides of the clot. Rather than be limited to reflective ultrasound imaging, through-transmission imaging can be performed by transmitting ultrasound from one transducer array and receiving the remaining unabsorbed ultrasonic energy at the other transducer array, which may reveal yet other characteristics of the brain tissue.

Figure 5:
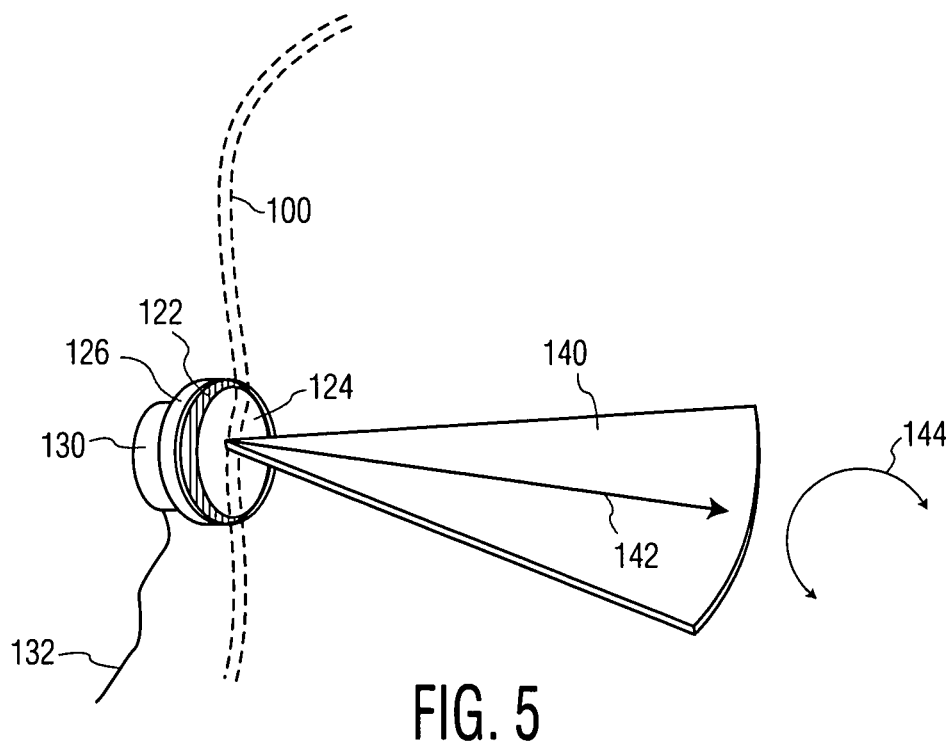
FIG. 5 illustrates two dimensional transcranial imaging in accordance with the present invention.

FIG. 5 illustrates a two dimensional imaging example of the present invention. In this example the transducer array 122 is a one dimensional array which performed 2D imaging. The array is configured as a circular phased array transducer as described in U.S. Pat. No. 5,226,422. This transducer array, like the other arrays described herein, is covered with a lens 124 which electrically insulates the patient from the transducer array and in the case of a one dimensional array may also provide focusing in the elevation (out-of-plane) dimension. The transducer array 122 is backed with acoustic damping material 126 which attenuates acoustic waves emanating from the back of the array to prevent their reflection back into the transducer elements. Behind this transducer stack is a device 130 for rotating the image plane 140 of the array. The device 130 may be a simple knob or tab which may be grasped by the clinician to manually rotate the circular array transducer in its rotatable transducer mount (not shown). The device 130 may also be a motor which is energized through a conductor 132 to mechanically rotate the transducer as discussed in U.S. Pat. No. 5,181,514 (Solomon et al.) Rotating the one dimensional array transducer 122 as indicated by arrow 144 will cause its image plane 140 to pivot around its central axis, enabling the repositioning of the image plane for full examination of the vasculature in front of the transducer array. As discussed in the '514 patent, the planes acquired during at least a 180° rotation of the array will occupy a conical volume in front of the transducer array, which may be rendered into a 3D image of that volumetric region. Other planes outside this volumetric region may be imaged by repositioning, rocking or tilting the transducer array in its headset in relation to the skull 100. If a stenosis is found in the image of the plane being imaged, the therapeutic beam vector graphic 142 can be steered by the clinician to aim the beam at the stenosis and therapeutic pulses applied to disrupt the microbubbles at the site of the stenosis.

It is common in the case of stroke that the affliction will not manifest itself in a single episode, but in repeated episodes as a blood clot or obstruction in the heart, lungs, or blood vessel breaks up gradually, releasing small clots which successively make their way to the vascular system of the brain over time. Thus, a patient who survives an initial stroke event, may be at risk for other events in the near future. Accordingly, it is desirable to monitor these patients for some time after an initial stroke event so that recurrences can be treated immediately. In accordance with a further aspect of the present invention, an embodiment of the invention may be used for the monitoring of stroke victims for recurrent events. The transducer arrays 10a,10b, microbeamformers 12a,12b, and multiplexer 14 can be efficiently packaged in a flip-chip configuration as part of the headset. These components can be battery powered and the output of the multiplexer connected to an r.f transmitter. A fixed image field 102,104 is continually imaged as shown in FIG. 4; it is not necessary to be able to steer or reposition the image field in this embodiment. The image data produced by the microbeamformers 12a,12b is wirelessly transmitted to a base unit as described in U.S. Pat. No. 6,113,547 (Catallo et al.) At the base station additional beamforming can be performed if necessary as well as the image processing and display functions of the system of FIG. 1. If a patient is not ambulatory a wireless connection may not be necessary and a wired connection to the base station may be employed. The wireless connection is also useful when the headset is being applied by individuals having minimal experience with the device. For example, a first responder may be unsure that the headset is applied properly and is acquiring a satisfactory image data set of the patient's vasculature. In that case the images can be transmitted to a base station, hospital or other location where experienced personnel can view the images in real time and talk the first responder through a successful application of the headset on the patient.

In the present example, image display is not necessary for the monitoring application. As successive images of the vasculature are formed at the base station they are stored in an image store 52, and temporally different images are compared to detect changes in flow of the vasculature by operation of flow change detector 50. The flow change detector operates by comparing the identical nature of the temporally different images, similar to the image data correlation techniques used to identify motion by image processing as described in U.S. Pat. No. 6,442,289 (Olsson et al.) As long as successive images and images separated by greater time intervals appear substantially the same in their flow characteristics, e.g., there is no localized change in the flow characteristics of a particular section of the vasculature and no section of the vasculature has ceased to return a Doppler signal indicating the continuation of flow, the flow change detector 50 will continue its monitoring of the vasculature with no change. For example, the vasculature may appear as the vascular network 300 of FIG. 6a for an extended period, and suddenly a section of the flow may cease to be detected as illustrated by the absence of vessels 302 in FIG. 6c. If a flow change such as one of those indicated above is detected by the flow change detector 50, an alarm is activated such as an audible alarm 42 at a nurse's station. Medical assistance can then be brought immediately to the patient. In addition, the images stored in the image store at the time of the detected flow change can be examined by medical personnel to discern exactly where in the vasculature the detected obstruction occurred. Therapy can then be directed specifically to the site of the obstruction without the need to closely examine a series of vascular maps.

Since this is a monitoring application, image acquisition does not have to be performed at the high rates necessary for real time imaging. A new image could be acquired every second, for example, or at greater intervals between image acquisitions. The lower acquisition rate is helpful for conserving battery power in an ambulatory implementation with an r.f. link. The lower image rate also permits images from multiple patients to be processed in a time-interleaved manner by the same system, which is useful for a nurse's station which needs to monitor multiple patients.

During long term monitoring or monitoring of ambulatory patients it is possible that the headset may move relative to the head of the patient, causing a difference between successive images from a transducer 10*a*, 10*b* which has moved. Such movement can also cause a specific anatomical region being monitored to move outside of the image field of the transducer array 10*a* or 10*b*. While the flow change detector 50 can be designed to be immune to such global changes and look only for localized changes in flow, it may be desirable to alert medical personnel to readjust the headset or to reacquire target anatomy in the image field. This is done in the embodiment of FIG. 1 by means of an image field controller 54, which performs image analysis of temporally different images to detect changes in global alignment of the image data. If the headset has not moved between successive images, for example, the successive images of each transducer array will be the same and the image data of the images will exhibit a high degree of correlation. The image analysis techniques used to measure image alignment in U.S. Pat. No. 5,556,674 (Weng), U.S. Pat. No. 6,572,549 (Jong et al.) or U.S. Pat. No. 6,589,176 (Jago et al.) and others may be used to perform the image comparison, for instance. Movement of the headset will result in a global change in correlation, which can alert medical personnel to adjust the headset. A local change in correlation may be a localized flow change that should be detected by the flow change detector 50 or the local decorrelation can be used to alert medical personnel to check the patient's condition. Another possibility is to use the global correlation vector as an indication of image-to-image motion. The motional change is then used by the transmit controller 18 to adjust the steering of beams of the image field 102, 104, 140 to relocate the anatomy in the same position in the newly acquired image field, as in the manner of image stabilization discussed in the aforementioned U.S. Pat. No. 6,589,176. This will enable the anatomy initially monitored by the system to remain in view and in the image data set despite small changes in the headset positioning. If the target anatomy moves beyond the range of beam steering reacquisition, an alert can be issued for medical personnel to reposition the headset. Such resteering correction in the presence of motion can similarly be used to keep the therapeutic pencil beam 110, 112 constantly directed at a targeted blood clot being treated.

Figure 7:
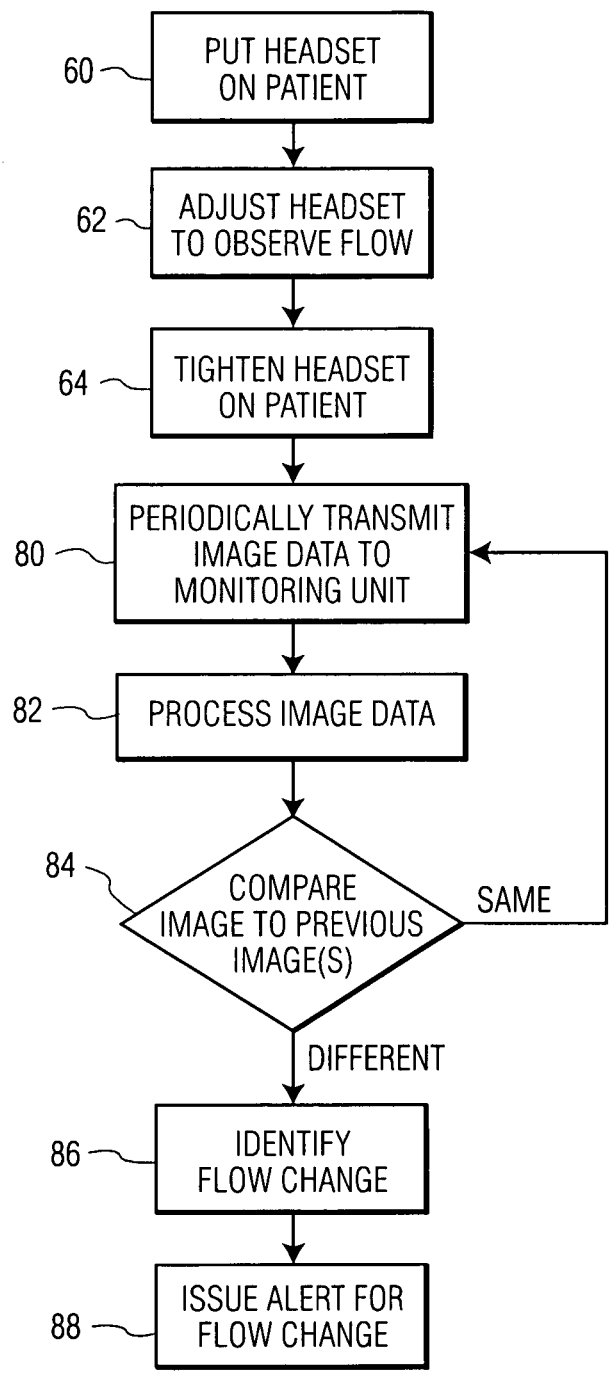
FIG. 7 illustrates a procedure for ultrasonically monitoring for cranial occlusions in accordance with the present invention.

A typical sequence for a monitoring implementation of the present invention is illustrated by the flowchart of FIG. 7. The headset with the array transducers is put on the patient at step 60 and images are initially displayed and reviewed until the headset is adjusted so that flow is observed in the images in step 62. When it is determined that images of cranial flow are being acquired, image display is no longer necessary and the headset is tightened in place on the patient at step 64. Periodically image data is acquired from the image field of the arrays and transmitted to the monitoring unit at step 80. At the monitoring unit the image data may be further processed as desired at step 82, then the new image is compared to one or more previously acquired images at step 84. If the flow characteristics of the images are unchanged, periodic transmission, reception, and comparison of image data continues. But if the new image is different in a predetermined flow characteristic, the flow change is detected at 86 and an alert issued at 88 for medical attention.

While the monitoring implementation can be performed with 2D (planar) imaging, it is preferred that 3D imaging be used so that a larger volumetric region can be monitored. Monitoring can be performed with only one transducer array, but a greater number of arrays likewise provides monitoring of a larger region of the cranium.

What is claimed is:

1. A stroke therapy system for treating cranial vascular obstructions comprising:
    a transducer array headset adapted to maintain an ultrasonic transducer array in acoustic contact with a head of a subject;
    a two dimensional array of transducer elements, located in the headset, the elements configured to steer both imaging beams and therapeutic beams over a volumetric region in the head of the subject;
    a microbeamformer, located in the headset and coupled to the elements of the two dimensional array of transducer elements;
    a transmit controller, coupled to the array of transducer elements, and configured to cause the elements to transmit beams in either an imaging mode or a therapy mode;
    an image processor, coupled to the microbeamformer, which is configured to produce harmonic images of microbubbles in the blood flow in the cranium of the subject when the elements are steering imaging beams over an imaged region of the cranium in the imaging mode;
    an image display, coupled to the image processor, which is configured to produce an image of the cranial vasculature; and
    a user control which is adapted to be manipulated by a user to aim a therapeutic beam vector on the image display at a location of an obstruction site in the image of the cranial vasculature,
    wherein the elements are caused to transmit a therapeutic beam of a duty cycle of 50% or less which is aimed along the therapeutic beam vector and focused at the obstruction site in the cranium of the subject to vibrate or break the microbubbles at the obstruction site when operated in the therapy mode.

2. The stroke therapy system of claim 1, wherein the image processor comprises a Doppler processor,
    wherein the Doppler processor is configured to produce at least one of colorflow Doppler images or power Doppler images.

3. The stroke therapy system of claim 1, wherein the two dimensional array of transducer elements is further configured to operate in the therapy mode to direct a therapeutic beam at the obstruction site in the cranium of the subject,
wherein the therapeutic beam comprises an ultrasonic beam which is capable of disrupting microbubbles at the obstruction site.

4. The stroke therapy system of claim 1, wherein the transducer array headset is adapted to maintain the two dimensional array of transducer elements in acoustic contact with one side of the head; and
further comprising a second two dimensional array of transducer elements located in the headset and adapted to be maintained in acoustic contact with the other side of the head by the headset.

5. The stroke therapy system of claim 4, wherein the first-named two dimensional array is configured to scan imaging beams over a majority of a cranial distance between the left side of the head and the center of the cranium; and
wherein the second two dimensional array is configured to scan imaging beams over a majority of a cranial distance between the right side of the head and the center of the cranium.

6. The stroke therapy system of claim 1, wherein the transmit controller further is configured to cause the two dimensional array of transducer elements to transmit beams in the imaging mode for at least one of Doppler or B mode imaging.

7. The stroke therapy system of claim 6, wherein the transmit controller further is configured to cause the transducer array to transmit beams for imaging over an image field exhibiting a given lateral dimension in the cranium,
wherein the therapeutic beam exhibits a lateral dimension which is less than the given lateral dimension.

8. The stroke therapy system of claim 6, wherein the transmit controller further is configured to transmit image beams over an image field occupying a given spatial region in the cranium,
wherein the therapeutic beam is transmitted over a portion of the given spatial region.

9. The stroke therapy system of claim 8,
wherein the given spatial region is a volumetric region.

10. A stroke therapy system for treating cranial vascular obstructions comprising:
a transducer array headset adapted to maintain an ultrasonic transducer array in acoustic contact with a head of a subject;
a one dimensional array of transducer elements, located in the headset, and configured to steer both imaging beams and therapy beams over a planar region in the head of the subject;
a device coupled to the array of transducer elements and configured for physically changing the planar region in the head which is imaged by the one dimensional array of transducer elements without disturbing the maintenance of acoustic coupling by the headset;
an image processor, coupled to the one dimensional array of transducer elements, which is configured to produce harmonic images of microbubbles in the blood flow in an image plane in the cranium of the subject;
an image display, coupled to the image processor, which is configured to produce an image of the cranial vasculature and the microbubbles;
a user control which is adapted to be manipulated by a user to align a displayed therapy beam vector at a location of an obstruction site in the image; and
a transmitter, coupled to the one dimensional transducer array, which is configured to cause the array of transducer elements to steer, focus, and transmit a therapeutic beam along the therapy beam vector at an energy which vibrates, oscillates, or ruptures the microbubbles at the obstruction site in the plane of the image,
wherein imaging and delivery of the therapeutic beam are done by a common one dimensional transducer array.

11. The stroke therapy system of claim 1, wherein imaging and the transmission of the therapeutic beam are both configured to be done within the limits for diagnostic ultrasound energy delivery to the subject.

12. The stroke therapy system of claim 10, wherein the transmitter is configured to apply at least one of pulse width modulated or duty cycle modulated signals to the transducer array.

13. The stroke therapy system of claim 10, wherein the one dimensional array is adapted to be maintained in acoustic contact with one side of the head;
further comprising a second one dimensional array which is adapted to be maintained in acoustic contact by the headset with the other side of the head.

14. A method for treating stroke comprising:
applying a headset containing first and second two dimensional arrays of transducer elements to the head of a subject with the transducer arrays in acoustic contact with opposite sides of the head;
producing a harmonic ultrasound image of cranial flow from signals received from at least one of the transducer arrays;
securing the headset to maintain the transducer arrays in acoustic contact with the head;
infusing the blood stream of the subject with microbubbles;
producing an ultrasound image of cranial flow containing microbubbles;
identifying the location of a stenosis in the ultrasound image;
manipulating a user control to align a therapy beam vector at the identified location of the stenosis in the image; and
transmitting a therapeutic ultrasound beam from one of the transducer arrays in the direction of the therapy beam vector and focused at the location of microbubbles imaged by the transducer array at the location of the stenosis and at an energy which vibrates or destroys the microbubbles at the location of the stenosis.

15. The method of claim 14, further comprising:
detecting a stenosis in the ultrasound image of cranial flow containing microbubbles; and
directing a therapeutic ultrasound beam from at least one of the transducer arrays to microbubbles proximal to the stenosis.

16. The method of claim 15 wherein directing the therapeutic ultrasound beam further comprises steering a pencil beam to microbubbles proximal to the stenosis.

17. The method of claim 15 wherein directing the therapeutic ultrasound beam further comprises vibrating microbubbles proximal to the stenosis.

18. The method of claim 15 wherein directing the therapeutic ultrasound beam further comprises breaking microbubbles proximal to the stenosis.

19. The method of claim 15, wherein directing the therapeutic ultrasound beam further comprises transmitting the therapeutic ultrasound beam to microbubbles proximal to the stenosis at an energy level which is within the limits for diagnostic ultrasound.

20. The method of claim 14,
wherein producing an ultrasound image further comprises producing a three dimensional ultrasound image.

* * * * *